United States Patent [19]

Sanderson et al.

[11] Patent Number: 5,132,465

[45] Date of Patent: Jul. 21, 1992

[54] OXIDATION OF PRIMARY ALCOHOLS TO ALDEHYDES USING TRANSITION METAL PHTHALOCYANINES AS CATALYSTS

[75] Inventors: John R. Sanderson, Leander; Edward T. Marquis, Austin, both of Tex.

[73] Assignee: Texaco Chemical Company, White Plains, N.Y.

[21] Appl. No.: 689,569

[22] Filed: Apr. 23, 1991

[51] Int. Cl.$^5$ .................. C07C 45/29; C07C 41/56
[52] U.S. Cl. ................ 568/485; 568/594; 568/487
[58] Field of Search ............ 568/487, 485, 488, 594, 568/672

[56] References Cited

U.S. PATENT DOCUMENTS 3,855,307 12/1974 Rony et al. ................ 568/454
4,978,799 12/1990 Sanderson et al. .......... 568/385

OTHER PUBLICATIONS

A. Streitwieser, Jr., *Introduction to Organic Chemistry*, Macmillan Publishing Co., New York, 1976, pp. 357, 391.

H. P. Kaufmann, et al., "Die Darstellung höherer Fettaldehyde", Chemische Berichte, vol. 91, 1958, pp. 2127–2129.

W. W. Epstein, et al., "Dimethyl Sulfoxide Oxidations", Chemical Reviews, vol. 67, No. 3, May 1967, pp. 247–260.

L. B. Young, et al., "Cerium (IV) Oxidation of Organic Compounds III. Preparation of Cyclopropanecarbaldehyde from Cyclopropanemethanol", *J. Org. Chem.*, vol. 32, 1967, pp. 2349–2350.

T. Takaya et al., "Novel Reactions of Iodosobenzene with Various Organic Compounds,"*Bull. Chem. Society of Japan*, vol. 41, No. 4, 1968, p. 1032.

C. A. Buehler, et al., *Organic Synthesis*, New York: Wiley–Interscience, 1970, pp. 542–555.

*Kirk–Othmer Encyclopedia of Chemical Technology*, Third Edition, vol. 1, New York: Wiley–Interscience, 1978, pp. 790–798.

P. L. Anelli, et al., "Fast and Selective Oxidation of Primary Alcohols to Aldehydes or to Carboxylic Acids and Use of Secondary Alcohols to Ketones Mediated by Oxoammonium Salts under Two-Phase Conditions", J. Org. Chem., 1987, vol. 52, pp. 2559–2562.

B. S. Furniss et al., ed., *Vogel's Textbook of Practical Organic Chemistry*, New York: Longman Scientific & Technical, 1987, pp. 414–424.

M. Hudlicky, "Oxidations in Organic Chemistry", ACS Monograph 186, 1990, pp. 114–126.

*Primary Examiner*—Marianne Cintins
*Assistant Examiner*—Michael B. Hydorn
*Attorney, Agent, or Firm*—Jack H. Park; Kenneth R. Priem; David L. Mossman

[57] ABSTRACT

Primary alcohols may be oxidized to the corresponding aldehydes using non-toxic oxidizing agents such as tert-butyl hydroperoxide (TBHP) in the presence of a transition metal phthalocyanine catalyst. Representative catalysts include ferrous phthalocyanine and chloroferric phthalocyanine. Under some conditions, 1,1-dialkoxyalkanes may be co-produced with the aldehydes. 1,1-Dialkoxyalkanes are protected aldehydes and find utility in solvents.

16 Claims, No Drawings

OXIDATION OF PRIMARY ALCOHOLS TO ALDEHYDES USING TRANSITION METAL PHTHALOCYANINES AS CATALYSTS

FIELD OF THE INVENTION

The invention relate to a method for oxidizing primary alcohols to aldehydes, and, in one aspect, more particularly relates to the oxidation of primary alcohols to aldehydes in the presence of an iron phthalocyanine catalyst.

BACKGROUND OF THE INVENTION

Aldehydes are well known useful compounds and are particularly useful as chemical intermediates, for example, to make the corresponding acids. Aldehydes of low molecular weight are condensed in an aldol reaction to produce derivatives used in the plasticizer industry. These materials are also used as intermediates for the manufacture of solvents, resins and dyes.

Numerous preparations are known for aldehydes. For example, M. Hudlicky, "Oxidations in Organic Chemistry," *ACS Monograph* 186, 1990, pp. 114–126 teaches the dehydrogenation and oxidation of primary alcohols to aldehydes using a variety of catalysts, including but not limited to, oxides of copper, cobalt and chromium; copper, silver and mixtures thereof; cupric oxide; platinum; platinum dioxide; ceric ammonium nitrate; sodium bromate; lead tetraacetate; hexavalent chromium; sodium or potassium dichromate; pyridinium dichromate; chromic acid; Jones reagent; Collins reagent; pyridinium chlorochromate; chromyl chloride; di-tert-butyl chromate; manganese dioxide; tetrachloro-o-benzoquinone; tetrachloro-p-benzoquinone; 2,3-dichloro-5,6-dicyano-p-benzoquinone; dimethyl sulfide and chlorine; N-chlorosuccinimide (NCS); dimethylsulfoxide (DMSO); and the like.

B. S. Furniss, et al., ed., *Vogel's Textbook of Practical Organic Chemistry*, New York: Longman Scientific & Technical, 1987, pp. 414–424 describe the preparation of a number of aldehydes, including the oxidation of primary alcohols to aldehydes including (1) oxidation of primary alcohols to the corresponding aldehyde using sodium dichromate; (2) butyraldehyde from butan-1-ol over sodium dichromate dihydrate; and (3) producing hexanal from hexanol using a catalyst of copper-chromium oxide deposited on pumice.

A number of oxidizing agents are shown as useful in the preparation of aldehydes including DMSO; ceric ammonium nitrate; chromium trioxide in dry pyridine, t-butyl chromate or dipyridine $Cr^{(VI)}$ oxide; potassium hypochlorite; iodosobenzene; chromic anhydride in dilute acetic acid; selenium dioxide; lead tetraacetate; and 1-chlorobenzo-triazole according to C. A. Buehler, et al., *Organic Synthesis*, New York: Wiley-Interscience, 1970, pp. 542–555.

See also *Kirk-Othmer Encyclopedia of Chemical Technology*, Third Edition, Vol. 1, New York: Wiley-Interscience, 1978, pp. 790–798. It indicates on page 795 that "The lower aldehydes may be prepared by oxidation of the corresponding alcohol with manganese dioxide or a sulfuric acid solution of potassium dichromate."

Primary alcohols are quantitatively oxidized to aldehydes in a few minutes at 0° C. in $CH_2Cl_2$-0.35M aqueous NaOCl in the presence of catalytic amounts of 4-methoxy-2,2,6,6-tetramethylpiperidine-1-oxyl according to P. L. Anelli, et al., "Fast and Selective Oxidation of Primary Alcohols to Aldehydes or to Carboxylic Acids and of Secondary Alcohols to Ketones Mediated by Oxoammonium Salts Under Two-Phase Conditions," *J. Org. Chem.*, 1987, Vol. 52, pp. 2559–2562. It was noted that cocatalysis by $Br^-$ and buffering of pH at 8.6 with $NaHCO_3$ are also required.

T. Takaya, et al. in "Novel Reactions of Iodosobenzene with Various Organic Compounds," *Bull. Chem. Society of Japan*, Vol. 41, No. 4, 1968, p. 1032, describe that a solution of an alcohol and iodosobenzene in dry dioxane gave the corresponding aldehydes. That DMSO is an oxidizing catalyst for the production of aldehydes is also seen in W. W. Epstein, et al., "Dimethyl Sulfoxide Oxidations," *Chemical Reviews*, Vol. 67, No. 3, May, 1967, pp. 247–260.

H. P. Kaufmann, et al., in "Die Darstellung höherer Fettaldehyde," *Chemische Berichte*, Vol. 91, 1958, pp. 2127–2129 teaches selenium dioxide as a catalyst for the oxidation of alcohols to aldehydes. The oxidation of cyclopropanemethanol to cyclopropanecarbaldehyde using an aqueous solution of 1N in ceric ammonium nitrate is described by L. B. Young, et al. in "Cerium-(IV) Oxidation of Organic Compounds. III. Preparation of Cyclopropanecarbaldehyde from Cyclopropanemethanol," *J. Org. Chem.*, Vol. 32, 1967, pp. 2349–2350.

The catalysts used in this invention, the iron phthalocyanines, are known to catalyze the production of detergent range alcohols and ketones from the corresponding alkanes according to U.S. Pat. No. 4,978,799.

While there are a plethora of syntheses for oxidizing primary alcohols to aldehydes, many of the catalysts used have significant disadvantages. For example, using DMSO gives toxic by-products, although DMSO itself is relatively safe. Iodosobenzene, ceric ammonium nitrate, chromium trioxide in pyridine, selenium dioxide and lead tetraacetate are all toxic materials. Iodosobenzene is additionally relatively expensive. There remains a need for a simple synthesis of aldehydes from primary alcohols that has little or no toxicity concerns and which employs relatively inexpensive catalysts.

SUMMARY OF THE INVENTION

Accordingly, it is an object of the present invention to provide a simple process for the production of aldehydes from primary alcohols.

It is another object of the present invention to provide a process for oxidizing alcohols to aldehydes which has little or no toxicity concerns relating to the catalyst or by-products.

Another object of the invention is to provide a method for catalytically oxidizing primary alcohols to aldehydes which produces a useful by-product.

In carrying out these and other objects of the invention, there is provided, in one form, a catalytic process for producing an aldehyde comprising reacting a primary alcohol with a hydroperoxide in the presence of a transition metal phthalocyanine catalyst.

DETAILED DESCRIPTION OF THE INVENTION

It has been discovered that primary alcohols may be oxidized to the corresponding aldehydes in the presence of a hydroperoxide and a transition metal phthalocyanine catalyst. Suitable hydroperoxide oxidizing agents include, but are not necessarily limited to, tert-butyl hydroperoxide (TBHP), cumene hydroperoxide, cyclohexyl hydroperoxide, ethylbenzene hydroperoxide, benzylhydroperoxide, cyclohexylbenzene hydroperoxide, and the like. TBHP is preferred; it is cheaper than most previously used oxidants; it is not toxic and does not produce a toxic by-product. It gives tert-butyl alcohol, which also has the advantage of not producing a noxious odor. The reaction of the invention may be diagrammed as shown in equation (I):

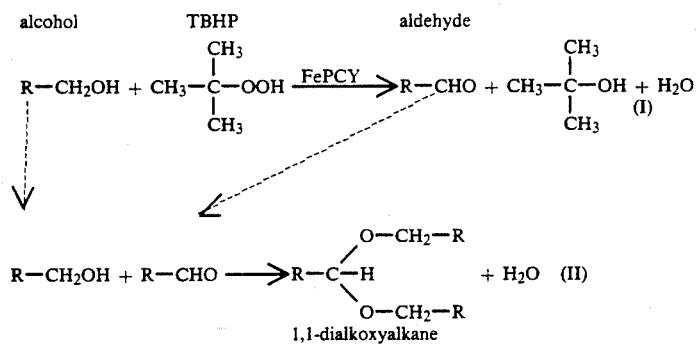

1,1-dialkoxyalkane

The alcohols have the formula R-CH$_2$OH, while the produced corresponding aldehyde has the corresponding formula R-CHO, where R represents a branched or straight alkyl group of 1 to 16 carbon atoms. For example, ethanol will give acetaldehyde. n-Butanol will give n-butanal.

An unusual aspect of the process of this invention is that 1,1-dialkoxyalkanes may be produced as a by-product as illustrated by reaction (II). These materials are useful as protected aldehydes and find utility in solvents. They are produced in good yields under some conditions. Production of the aldehyde v. the 1,1-dialkoxyalkanes (selectivity) is controlled by the time and temperature of the reaction. The relatively longer and/or the hotter the reaction is permitted to proceed, the greater is the selectively to the 1,1-dialkoxyalkane.

The catalysts useful in the process of the invention are transition metal phthalocyanines. Suitable catalysts include, but are not necessarily limited to ferrous phthalocyanine, chloroferric phthalocyanine, cobalt phthalocyanine, manganese phthalocyanine, copper phthalocyanine and mixtures thereof. In particular, ferrous phthalocyanine, chloroferric phthalocyanine and mixtures thereof are particularly preferred. Ligands may be optionally used with the catalyst. Suitable ligands include, but are not limited to imidazoles, methyl-imidazoles, pyridines, methyl-pyridines, and the like. The use of ligands in this reaction will generally increase reactivity.

The reaction may be conducted in batch or continuously at atmospheric or elevated pressures. The suitable temperature is from about 10° to about 100° C. In one aspect, a preferred temperature range is from about 15° to abut 35° C. At temperatures much above 100° C., conversions to dicarboxylic acids via the 1,1-dialkoxyalkanes will result.

The invention will be further illustrated by the following examples which are provided for additional understanding and not to limit the scope of the invention.

EXAMPLE 1

Oxidation of Ethanol to Acetaldehyde

Ethanol (18.0 g., 95%) and chloroferric phthalocyanine (0.20 g.) were charged to a 250 ml round bottomed flask equipped with a magnetic stirrer, water bath, thermometer, and addition funnel. The 90% tert-butyl hydroperoxide (TBHP)(5.0 g.) was added all at once (exotherm to 30°-35° C.). The mixture was stirred for 15 hours and the temperature maintained at 25° C. ±5° C. The solid was then filtered off, and the liquid products analyzed by gas chromatography (GC). The following products were observed, expressed as wt. % of the total product. The balance of the total product were unreacted materials.

| Acetaldehyde | 1.5 wt. % |
|---|---|
| tert-Butyl alcohol | 23 |
| Ethyl acetate | 1.1 |
| Acetal | 15 |

EXAMPLE 2

Oxidation of Ethanol to Acetaldehyde

Ethanol (18.0 g., 100%) and ferrous phthalocyanine (0.20 g.) were charged to a 250 ml round bottomed flask equipped with a magnetic stirrer, water bath, thermometer, and addition funnel. The 90% TBHP (5.0 g.) was added slowly to the stirred reaction mixture. The temperature maintained at 25° C. ±5° C. The mixture was stirred over the weekend at 25° C. ±5° C., the solid was filtered off, and the liquid products analyzed by GC. The following products were observed.

| Acetaldehyde | 3.3 wt. % |
|---|---|
| Acetone | 0.43 |
| Acetal | 0.5 |

EXAMPLE 3

Oxidation of Ethanol to Acetaldehyde

The procedure of Example 2 was followed herein except that chloroferric phthalocyanine (0.20 g.) and imidazole (0.10 g.) were charged as the catalyst. The following products were observed by GC.

| Acetaldehyde | 3.8 wt. % |
|---|---|
| Acetone | 0.5 |
| Acetal | 0.6 |

EXAMPLE 4

Oxidation of n-Butanol to n-Butanal n-Butanol (18.0 g.) and chloroferric phthalocyanine (0.20 g.) were charged to a 250 ml round-bottomed flask equipped with a magnetic stirrer, water bath, thermometer and addition funnel. TBHP (5.0 g., 90%) was added slowly to the stirred reaction mixture. The temperature was maintained at 25° C. ±5° C. The mixture was then stirred at 25° C. ±5° C. for 15 hours, the solid was then filtered off and the liquid analyzed by GC/infrared (IR) and GC/mass spectroscopy (MS). The following products were observed.

| | |
|---|---|
| n-Butanal | 4 wt. % |
| tert-Butanol | 15 |
| Butanoic acid, n-butyl ester | 0.7 |
| Butanoic acid | 1.5 |

It will be appreciated that the yields to the aldehydes and/or 1,1-dialkoxyalkanes are not optimized. Many modifications may be made in the process of this invention without departing from the spirit and scope thereof which are defined only in the appended claims. For example, one skilled in the art may discover that a certain combination of transition metal phthalocyanine and ligand may give particularly advantageous results.

I claim:

1. A catalytic process for producing an aldehyde comprising reacting a primary alcohol with a hydroperoxide in the presence of a transition metal phthalocyanine catalyst wherein the primary alcohol has the formula $RCH_2OH$ and the aldehyde has the formula RCHO where R represents a straight or branched alkyl group having from 1 to 16 carbon atoms.

2. The process of claim 1 where the catalyst is selected from the group consisting of chloroferric phthalocyanine, ferrous phthalocyanine, cobalt phthalocyanine, manganese phthalocyanine, copper phthalocyanine, and mixtures thereof.

3. The process of claim 1 where the catalyst is selected from the group consisting of chloroferric phthalocyanine, ferrous phthalocyanine and mixtures thereof.

4. The process of claim 1 where the catalyst is an iron phthalocyanine and a ligand is present for the iron phthalocyanine catalyst, where the ligand is selected from the group consisting of imidazole, methylimidazole, pyridine, and methyl-pyridine.

5. The process of claim 1 conducted at a temperature in the range of about 10° to about 100° C.

6. The process of claim 1 conducted at a temperature in the range of about 15° to about 35° C.

7. The process of claim 1 where the hydroperoxide is selected from the group consisting of tert-butyl hydroperoxide (TBHP), cumene hydroperoxide, cyclohexyl hydroperoxide, ethylbenzene hydroperoxide, benzylhydroperoxide and cyclohexylbenzene hydroperoxide.

8. The process of claim 1 where the hydroperoxide is tert-butyl hydroperoxide (TBHP).

9. A catalytic process for producing an aldehyde comprising reacting a primary alcohol having the formula $RCH_2OH$ and the aldehyde has the formula RCHO where R represents a straight or branched alkyl group having from 1 to 16 carbon atoms, with a hydroperoxide selected from the group consisting of tert-butyl hydroperoxide (TBHP), cumene hydroperoxide, cyclohexyl hydroperoxide, ethylbenzene hydroperoxide, benzylhydroperoxide and cyclohexylbenzene hydroperoxide, in the presence of a transition metal phthalocyanine catalyst selected from the group consisting of chloroferric phthalocyanine, ferrous phthalocyanine, cobalt phthalocyanine, manganese phthalocyanine, copper phthalocyanine, and mixtures thereof at a temperature in the range of about 10° to about 100° C.

10. The process of claim 9 where the catalyst is selected from the group consisting of chloroferric phthalocyanine, ferrous phthalocyanine and mixtures thereof.

11. The process of claim 9 where the catalyst is an iron phthalocyanine and a ligand is present for the iron phthalocyanine catalyst, where the ligand is selected from the group consisting of imidazole, methylimidazole, pyridine, and methyl-pyridine.

12. The process of claim 9 conducted at a temperature in the range of about 15° to about 35° C.

13. The process of claim 9 where the hydroperoxide is tert-butyl hydroperoxide (TBHP).

14. A catalytic process for co-producing an aldehyde having the formula RCHO and a 1,1-dialkoxyalkane having the formula $R-CH-(OCH_2-R)$ where R represents a straight or branched alkyl group having from 1 to 16 carbon atoms, comprising reacting a primary alcohol having the formula $RCH_2OH$ with tert-butyl hydroperoxide (TBHP) in the presence of an iron phthalocyanine catalyst selected from the group consisting of chloroferric phthalocyanine, ferrous phthalocyanine and mixtures thereof, at a temperature in the range of about 10° to about 100° C.

15. The process of claim 14 where a ligand is present for the iron phthalocyanine catalyst, where the ligand is selected from the group consisting of imidazole, methyl-imidazole, pyridine, and methyl-pyridine.

16. The process of claim 14 conducted at a temperature in the range of about 15° to about 35° C.

* * * * *